(12) United States Patent
Sokolov et al.

(10) Patent No.: US 10,509,040 B2
(45) Date of Patent: Dec. 17, 2019

(54) METHOD FOR MEASURING GLYCEMIC INDEX OF HUMAN-CONSUMED FOOD

(71) Applicant: Healbe Corporation, Redwood City, CA (US)

(72) Inventors: Evgeny L. Sokolov, Leningradskaya obl. (RU); Andrey A. Chechik, St. Petersburg (RU); Vladimir Yu. Elokhovskiy, St. Petersburg (RU); Dmitry I. Kolonitsky, St. Petersburg (RU)

(73) Assignee: Healbe Corporation, Redwood City, CA (US)

( * ) Notice: Subject to any disclaimer, the term of this patent is extended or adjusted under 35 U.S.C. 154(b) by 76 days.

(21) Appl. No.: 15/703,290

(22) Filed: Sep. 13, 2017

(65) Prior Publication Data

US 2018/0074069 A1    Mar. 15, 2018

Related U.S. Application Data

(63) Continuation of application No. PCT/RU2016/000099, filed on Feb. 24, 2016.

(30) Foreign Application Priority Data

Mar. 13, 2015 (RU) ................................ 2015108820

(51) Int. Cl.
*G01N 33/50* (2006.01)
*G01N 33/66* (2006.01)
*A61B 5/145* (2006.01)

(52) U.S. Cl.
CPC ......... *G01N 33/66* (2013.01); *A61B 5/14532* (2013.01); *G01N 2400/00* (2013.01)

(58) Field of Classification Search
CPC . G01N 33/66; G01N 2400/00; A61B 5/14532
See application file for complete search history.

(56) References Cited

U.S. PATENT DOCUMENTS

| | | |
|---|---|---|
| 2004/0043106 A1 | 3/2004 | Anfinsen et al. |
| 2005/0244910 A1 | 11/2005 | Wolever et al. |
| 2005/0266385 A1 | 12/2005 | Bisogno |
| 2011/0053121 A1 | 3/2011 | Heaton |

FOREIGN PATENT DOCUMENTS

| | | |
|---|---|---|
| CN | 101784898 A | 7/2010 |
| CN | 102405011 A | 4/2012 |
| EP | 2006786 A1 | 12/2008 |
| EP | 1660889 B1 | 5/2011 |
| RU | 2451938 C2 | 5/2012 |
| WO | 2002/05702 A2 | 1/2002 |
| WO | 2005/017532 A1 | 2/2005 |
| WO | 2008/009737 A2 | 1/2008 |
| WO | 2013/125987 A1 | 8/2013 |

OTHER PUBLICATIONS

Dodd, Hayley et al. "Calculating meal glycemic index by using measured and published food values compared with directly measured meal glycemic index." American Journal of Clinical Nutrition (2011) 94 992-996. (Year: 2011).*

Vashist, Sandeep Kumar. "Non-invasive glucose monitoring technology in diabetes management: A review." Aanlytica Chimica Acta (2012) 750 16-27. (Year: 2012).*

Jenkins et al., Glycemic index of foods: a physiological basis for carbohydrate exchange, the American Journal of Clinical Nutrition, Mar. 1981, pp. 362-366, vol. 34, American Society for Clinical Nutrition.

Brand-Miller et al, Glycemic index, postprandial glycemia, and the shape of the curve in healthy subjects: analysis of a database of more than 1000 foods., Am. J. Clin. Nutr. 2009, pp. 97-105, vol. 89, American Society for Nutrition.

International Search Report from International Application No. PCT/RU2016/000099, filed Feb. 24, 2016, dated Aug. 11, 2016.

Foster-Powell, et al., International table of glycemic index and glycemic load values, 2002, Am. J. Clin Nutr, 2002, pp. 5-56, v. 76, American Society for Clinical Nutrition.

Ihediohanma, Determination of the Glycemic Indices of Three Different Cassava Granules (Garri) and the Effect of Fermentation Period on Their Glycemic Responses, Pakistan Journal of Nutrition, 2011, pp. 6-9, v. 10, No. 1.

Venn B. J. et al. The use of different reference foods in determining the glycemic index of starchy and non-starchy test foods, Nutrition Journal, 2014, 13:50.

Elliott R. M. et al, Glucagon-like peptide-1(7-36)amide and glucose-dependent insulinotropic polypeptide secretion in response to nutrient ingestion in man: acute post-prandial and 24-h secretion patterns. Journal of Endocrinology, 1993, v. 138, pp. 159-166.

Belyaev et al, Noninvasive Monitoring of Glucose—Key Resource Optimization of Treatment of Sugar Diabetes, Abstracts of the All-Russian Conference with International Participation "Translational Research in Innovative Health Development", Appendix 1. May 2014, p. 7.

(Continued)

*Primary Examiner* — Christopher Adam Hixson
(74) *Attorney, Agent, or Firm* — Patentbar International P.C.

(57) ABSTRACT

The glycemic index is determined based on the results of blood glucose concentration measurements by evaluating time $\Delta t$ from the beginning of food-related increase of blood glucose concentration until the peak of glucose concentration is reached, after which maximum increase $\Delta G_{max}$ of said glucose concentration is determined over the given period of time. Thereat, the glycemic index of food is defined as a ratio of maximum increase of blood glucose concentration $\Delta G_{max}$ versus maximum increase of said glucose concentration in case of pure glucose intake in the amount equal to carbohydrate content of the consumed food, which is proportional to the product of $\Delta G_{max}$ by $\Delta t$. The invention substantially simplifies the procedure for measuring the glycemic index of real food and facilitates the development of simple personal devices for monitoring carbohydrate metabolism.

4 Claims, 2 Drawing Sheets

(56) References Cited

OTHER PUBLICATIONS

Brand-Miller J. et al., The glucose revolution: the authoritative guide to the glycemic index, the groundbreaking medical discovery, Marlow & Company, New York, 1999, Chapter 2, p. 33.
Wu Fuyou, Obesity and body remodeling physiology, Bejing: China Light Industry Press, Sep. 30, 2012, pp. 138-140.
Liu Huiying et al, Research progress on food glycemic index and its prediction model, Practical Preventive Medicine, Feb. 28, 2014, vol. 21, No. 2.
First Office Action by the State Intellectual Property Office of China, on Application No. 201680026245.9, dated Sep. 14, 2018.

* cited by examiner

METHOD FOR MEASURING GLYCEMIC INDEX OF HUMAN-CONSUMED FOOD

RELATED APPLICATIONS

This Application is a Continuation application of International Application PCT/RU2016/000099, filed on Feb. 24, 2016, which in turn claims priority to Russian Patent Applications No. RU 2015108820, filed Mar. 13, 2015, both of which are incorporated herein by reference in their entirety.

FIELD OF INVENTION

The invention relates to the field of measurements for diagnostic purposes, in particular to measurements made to assess the effect of nutrient load upon human body. It can be used to develop simple personal technical means to monitor food intake based on human body response to consumed food.

BACKGROUND OF THE INVENTION

The glycemic index is a value that measures the variation of blood glucose (blood sugar) concentration by showing how fast and to what level the blood glucose concentration increases during intake of particular food. The glycemic index demonstrates the rate with which a certain food converts into glucose and infiltrates the blood.

The glycemic index of a particular food product is a relative notion. It is based on the index of pure glucose, which is assumed to be 100. The glycemic index of other food products ranges from 0 to 100 depending on the rate of its absorption by human body. Food products with a high glycemic index induce a rapid increase of blood glucose concentration. They are easily digested and absorbed by human body. Food products with a lower glycemic index cause a tempered increase of blood glucose concentration, because carbohydrates that they contain are digested more slowly.

The glycemic index is defined as a ratio of the area under the so-called glycemic response curve, which shows the variation of blood glucose concentration from the time a meal was taken until the moment it gets completely assimilated by human body, to the area under a similar glycemic curve that reflects the intake of pure glucose equal in amount to the amount of carbohydrates contained in a given food product.

The glycemic index usually refers to a certain food product. A series of tests are conducted to record the glycemic curve observed when a test subject consumes a food product with a known amount of glucose. In other experiments, the same test subject consumes an equal amount of pure glucose. As a result, average values of said ratios are obtained for the areas under glycemic curves. The glycemic index is usually expressed as a percentage.

For practical purposes, tables of glycemic indices are compiled for various food products. An exemplary table is shown in: Kaye Foster-Powell, Susanna H A Holt, and Janette C Brand-Miller. International table of glycemic index and glycemic load values: 2002. Am J Clin Nutr.— 2002, 76, 5-56.

However, such information on glycemic indices for particular food products can be insufficient for people, who, for example, follow a diet, in particular, monitor their glucose assimilation. Since the assimilation of food is individual for each person, they would like to know the glycemic index for specific food products they consume, rather than averaged data for separate products. In addition, they would like to know the glycemic index of the entire food they consume, consisting of a diverse set of food products, rather than the glycemic index of individual food products. And most important, an average consumer wants to know the glycemic index of food right after its assimilation instead of running experiments with food and pure glucose.

Initially, methods based on consumer's assessment of the effect of food-related carbohydrates using special tables based on experimental studies were widely used. Using the tables of glycemic indices of particular food products, a consumer can find a numerical value of the glycemic index, which characterizes the reaction of human body to carbohydrates incoming with meal. This calculation can be performed using remote databases that recognize the images of consumed food products transmitted from consumer's mobile devices. Such an approach provides only a rough evaluation of the glycemic index, because it refers to a specific food product, rather than to actually cooked food; besides the individual reaction of the body to this food is left out of consideration.

Application U.S. 2005/0266385 (published on Jan. 12, 2005, IPC A23L1/29) describes a method for monitoring the nutrition content information of consumables, and is intended to facilitate menu planning. The glycemic index of consumables is measured using the known glycemic indices for particular food products. This method does not provide for the evaluation of the glycemic index of food composed of different products.

Application WO 2008/009737 (published on 24 Jan. 2008, IPC A61B05/00) describes a method for glycemic index evaluation based on glycemic indices for particular food products, said indices being transmitted from a remote database to consumer's personal device. Based on the glycemic indices of individual food products, which compose consumer's meal, and their amount, the glycemic index of entire meal is calculated.

The method closest to the claimed invention measures the glycemic index of consumed food generating a feedback as described in international application WO 2002/005702 (published on Dec. 9, 2002, IPC A61B5/00). The core of the method is that the information on food to be taken at a meal, including its glycemic index and amount, is fed into computer beforehand. After the meal, blood glucose concentration is measured using one of the known methods. Based on the calculated values of blood glucose concentration, the glucose curve is modified and the glycemic index of the consumed food is adjusted in regard to a specific person. The resulting data are used to predict the blood glucose concentration and warn about its inadmissible increase, necessity to change eating behavior or undergo treatment.

The disadvantages of this method include the need to run multiple experiments in order to evaluate the glycemic index for each food product, which is inconvenient, since it requires multiple calculations and repetitive consumption of a certain product under the same conditions. This method cannot guarantee a stable, reproducible evaluation of the glycemic index for the same food product.

So, the need for a sufficiently fast and simple method of evaluating the glycemic index for a variety of food products, including meals of complex composition, is still actual. Additionally, this method needs to take into account the individual food assimilation features of a particular person and must provide sufficient accuracy.

SUMMARY OF THE INVENTION

The technical task that the claimed invention is supposed to solve is the development of a method for evaluating the glycemic index of food that produces effect immediately after the meal is consumed, enables the evaluation of the glycemic index for real multicomponent food and takes into account physiological peculiarities of a person.

A method for evaluating the glycemic index of human-consumed food in accordance with the claimed invention that includes the following steps:

measurement of human blood glucose concentration in time, at least from the onset of blood glucose concentration rise caused by food intake and until its peak is reached, based on the above measurement, time interval $\Delta t$ from the onset of said food-related rise of blood glucose concentration to said concentration peak is evaluated and the maximum increase of blood glucose concentration $\Delta G_{max}$ over the given time period $\Delta t$ is specified, here, the glycemic index of consumed food is defined as a ratio of the maximum increase of blood glucose concentration $\Delta G_{max}$ to the maximum increase in blood glucose concentration upon intake of pure glucose equal in amount to carbohydrate content of the consumed food; said ratio being proportional to the product of $\Delta G_{max}$ by $\Delta t$.

The inventors have established experimentally that the area under the glycemic response curve G(t) within the limits between the onset of food-related blood glucose concentration rise and peak of glucose concentration $G_{max}$, when calculated without the initial value of glucose concentration taken into account, is proportional, with insignificant assumptions, to the amount of carbohydrates $C_{sum}$ that the consumed food contains. Given an almost linear nature of the blood glucose concentration rise over a given time interval $\Delta t$, the area under the glycemic response curve within the above-mentioned time limits and, as stated previously, without initial blood glucose concentration taken into account, would be equal to:

$$S=0.5 \cdot \Delta t \cdot \Delta G_{max},$$

where $\Delta G_{max}$ is the maximum increase of glucose concentration over time $\Delta t$.

In other words, the carbohydrate content of the consumed food is:

$$C_{sum}=K \cdot \Delta t \cdot \Delta G_{max}, \quad (1)$$

where K is a proportionality factor, the magnitude and dimension of which are determined experimentally with the dimensions that were used for $\Delta G_{max}$ and $\Delta t$ taken into account.

In reference to the maximum increase of blood glucose concentration, caused by pure glucose intake Gl equal in its amount to carbohydrate content $C_{sum}$ of the consumed food (let us denote the increase as $\Delta G_{max}^{(gl)}$), it can be estimated based of known data. For example, the data on blood glucose concentration increase following the intake of pure glucose can be found in:

Jennie C Brand-Miller, Karola Stockmann, Fiona Atkinson, Peter Petocz, and Gareth Denyer. Glycemic index, postprandial glycemia, and the shape of the curve in healthy subjects: analysis of a database of more than 1000 foods. *Am J Clin Nutr.* 2009, 89, 97-105.

R. M. Elliott, L. M. Morgan, J. A. Tredger, S. Deacon, J. Wright, and V. Marks. Glucagon-like peptide-1(7-36)amide and glucose-dependent insulinotropic polypeptide secretion in response to nutrient ingestion in man: acute post-prandial and 24-h secretion patterns. *J Endocrinol.*—1993, 138, 159-166.

Finally, the target value of glycemic index GI of human-consumer food is defined as a ratio of $\Delta G_{max}$ to $\Delta G_{max}^{(gl)}$, namely:

$$GI=(\Delta G_{max}/\Delta G_{max}^{(gl)}) \cdot 100. \quad (2)$$

Here, said ratio, when multiplied by 100, transforms the obtained value of the glycemic index to its conventional form.

Thus, the method described in the claimed invention makes it possible (1) to evaluate the glycemic index of consumed food having an arbitrary (multicomponent or complex) composition, i.e., of real food, and (2) to avoid complex calculations needed for separate assessment of food products comprising the consumed meal, evaluation of their glycemic indices and e total value of the glycemic index of the entire consumed meal. In reference to the measurement of blood glucose concentration G(t), current methods, primarily, non-invasive ones, (1) afford opportunity to make real time measurements at a frequency providing a reliable identification of a point in time when the growth of food-related blood glucose concentration stops, and, (2) are quite comfortable for users.

Experiments demonstrated that the above assumptions related to the evaluation of carbohydrate content $C_{sum}$ of the consumed food through $\Delta G_{max}$ and $\Delta t$ specified on the basis of blood glucose measurements G(t) may introduce errors of several percent into the results of glycemic index evaluation GI, which is considered quite acceptable for such measurements.

In a particular case of measuring carbohydrate content $C_{sum}$ of the consumed food, in grams, and specifying said time interval $\Delta t$, in min, and said maximum increase of blood glucose concentration $\Delta G_{max}$, in mmol/l, the proportionality factor K in equation (1) is selected within 0.35 g/min·mmol/l to 0.60 g/min·mmol/l range. The above values have been obtained experimentally by the inventors.

Specifically, when implementing this method using said quantity dimensions of measured values $\Delta G_{max}$, $\Delta t$ and factor value K, the maximum increase of blood glucose concentration $\Delta G_{max}^{(gl)}$ in case of pure glucose intake Gl equal in amount to carbohydrate content $C_{sum}$ of the consumed food can be determined using the plot shown in FIG. 1. This plot is also based on experiments.

As it was noted above, non-invasive measurements are preferable for the evaluation of blood glucose concentration.

BRIEF DESCRIPTION OF DRAWINGS

The invention is illustrated by the following graphic materials.

DISCLOSURE OF INVENTION

The method according to the present invention is implemented as follows. Measurement of blood glucose concentration G(t) starts when food intake begins. Any suitable methods and devices can be used for this purpose, with non-invasive methods being preferable, since the method proposed by the claimed invention involves repeated measurements of blood glucose concentration, and non-invasive methods are the most comfortable for humans. The measurements are performed continuously or over certain periods of time, which provides a sufficient reliably of evaluating changes in blood glucose concentration over time t. Due to food intake, blood glucose concentration of the consumer starts growing and reaches its maximum value after a certain period of time. Thereafter, the glucose concentration starts to decrease, which gives a signal to stop the measurement.

Based on the results of measurements, time interval Δt (in min) from the beginning of food-related rise of blood glucose concentration until its peak is reached, as well as the maximum increase of glucose concentration $\Delta G_{max}$ (in mmol/l) over a given period of time Δt are evaluated.

Further on, carbohydrate content $C_{sum}$ (in grams) of the food consumed during a meal is calculated using formula (1), with the proportionality factor K taken to be 0.525 g/min·mmol/l, which represents the average value for a healthy adult (see examples below).

Figure 1:
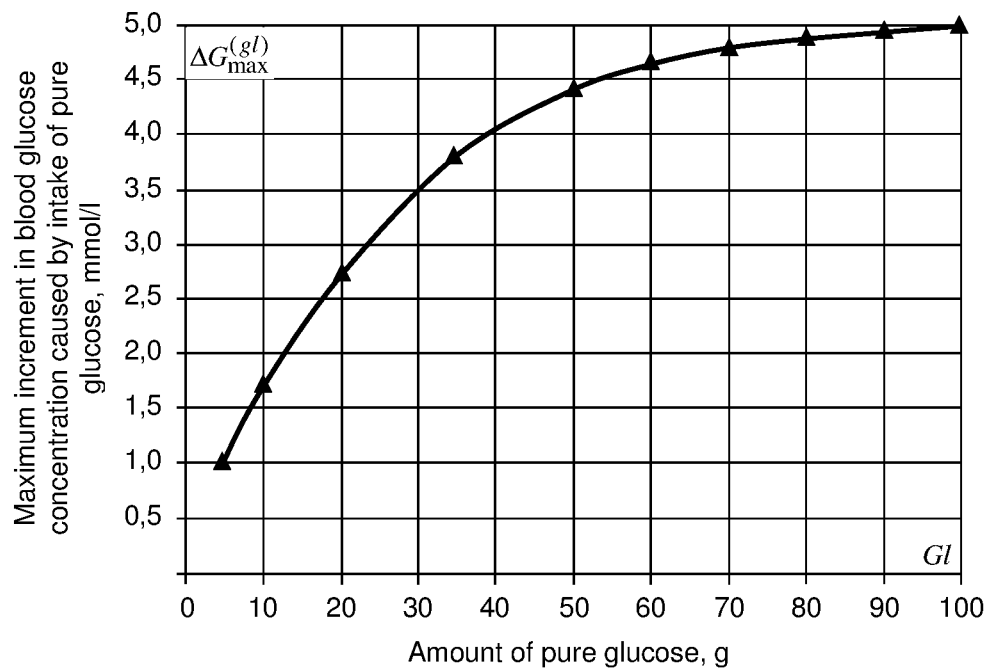
FIG. 1 shows the dependence of maximum increase of blood glucose concentration $\Delta G_{max}^{(gl)}$ related to the intake of pure glucose Gl, said dependence being experimentally determined by the inventors and used for implementing the proposed method.

Based on the specific value $C_{sum}$ and using the plot shown in FIG. 1, the maximum food-related increase of glucose concentration $\Delta G_{max}^{(gl)}$ caused by an intake of pure glucose Gl equal in amount to $C_{sum}$ is determined. This plot is based on experiments run by the authors of the method in the process of its development. The plot can be substituted either with a mathematical relationship representing an approximation of said curve, or with available experimental data.

Finally, the glycemic index GI of consumed food is determined from equation (2) as a ratio of the maximum increase of blood glucose concentration $\Delta G_{max}$ to value $\Delta G_{max}^{(gl)}$, which represents the maximum increase in blood glucose concentration in case of pure glucose intake.

As it was said, the method proposed in the claimed invention makes it possible to evaluate the glycemic index for specific food products, as well as their combination consumed during a meal, i.e., the glycemic index of mixed food load. The latter is of major interest for practical glycemic index evaluation, since the food consumed in everyday life is composed of various products.

DETAILED DESCRIPTION OF THE PREFERRED EMBODIMENTS

A number of experiments were undertaken to test the feasibility of the proposed method and to achieve said results. At each experiment, a volunteer received a dosed nutritional load consisting of different food products. In accordance with the claimed invention, volonteer's blood glucose concentration was measured from the beginning of the meal until the food-related growth of glucose concentration stopped. The glucose concentration was measured using the non-invasive method described in Application PCT/RU2013/000144 (International Publication Number WO 2013/125987). The measurements were made in 1 minute periods, with the results of measurements confirmed by standard invasive method with blood samples taken every 15 minutes. The results of the discrete measurements were recorded, and curves showing the relation of time t versus blood glucose concentration G were plotted using approximation (see FIG. 2-FIG. 4).

Based on the plotted curves, time interval Δt, within which blood glucose concentration growth G was observed, and maximum increase of glucose concentration $\Delta G_{max}$ over said time interval were estimated. Using equation (1), carbohydrate content $C_{sum}$ of the consumed food was calculated after which, drawing on the plot shown in FIG. 1, the maximum increase of blood glucose concentration $\Delta G_{max}^{(gl)}$ was evaluated for a case of pure glucose intake Gl; and the glycemic index of the consumed food was calculated using equation (2).

To confirm the results, a known method for calculating the total (or cumulative) glycemic index of mixed food was used. This method is described in book: The glucose revolution: the authoritative guide to the glycemic index, the groundbreaking medical discovery/by Jennie Brand-Miller at al.—Marlow & Company, New York, 1999, p. 33. In this method, carbohydrate content (in grams) of the consumed food is calculated, and, based thereon, the proportion of carbohydrate content in a given food product in the total nutritional load is determined. Thereafter, the glycemic index of each food product is multiplied by its specific carbohydrate content proportion, with the results are summed up to yield the total glycemic index of the nutritional load GI, or:

$$GI = \sum_{j=1}^{n} P_j \cdot GI_j,$$

where: $P_j$ is the carbohydrate content of j-th food product;
$GI_j$ is the glycemic index of j-th food product;
n is the number of individual food products that make up the mixed meal.

The glycemic indices of individual food products were taken from tables published in: Kaye Foster-Powell, Susanna H A Holt, and Janette C Brand-Miller. International table of glycemic index and glycemic load values: 2002. Am J Clin Nutr.—2002, 76, 5-56.

At the end of the experiments, the deviation of the total glycemic index value of the nutritional load (consumed food), obtained by the proposed method, from the cumulative glycemic index of the same nutritional load calculated using the control method was evaluated.

Example 1

Volunteer: a female, age 50, height 164 cm, weight 63 kg.
Composition of nutritional load:
Cream puff—65 g (carbohydrates—39.0 g, glycemic index (GI)—75);
Eclair—69 g (carbohydrates—20.7 g, GI—75);
Tea—200 ml, with granulated sugar—10 g (carbohydrates—10 g, GI—70).

Table 1.1 below shows the initial data and calculated value of consumed food glycemic index obtained using the confirmatory method.

TABLE 1.1.

| Food composition | Carbohydrates, g | Carbohydrate content | Product GI | Contribution to mixed nutritional load GI |
|---|---|---|---|---|
| Cream puff | 39.0 | 0.56 | 75 | 0.56 · 75 = 42.0 |
| Eclair | 20.7 | 0.30 | 75 | 0.30 · 75 = 22.5 |
| Tea with granulated sugar | 10.0 | 0.14 | 70 | 0.14 · 70 = 9.8 |
| Total | 69.7 | 1.0 | | 74.3 |

The calculation of glycemic index in accordance with the claimed invention yielded the following results.

Figure 2:
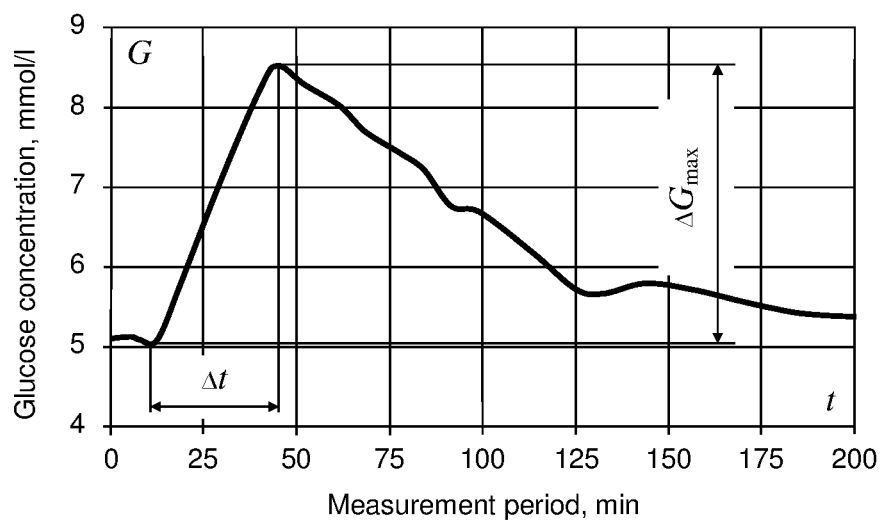
FIG. 2 shows blood glucose concentration measurement results for the first implementation of the invention.

FIG. 2 shows a plot of blood glucose concentration values G measured from the beginning of food intake, which enables the evaluation of:

time lapse $\Delta t=37$ minutes, during which an increase in glucose concentration was observed, and maximum increase of glucose concentration $\Delta G_{max}=3.4$ mmol/l over said time period $\Delta t$.

Using equation (1), the carbohydrate content $C_{sum}$ of the food consumed during a meal was calculated and found equal to $C_{sum}=66.0$ g, with factor K assumed to be 0.525 g/min·mmol/l.

The maximum increase of blood glucose concentration that would occur in case of pure glucose intake was determined from the plot shown in FIG. 1 and found $\Delta G_{max}^{(gl)}=4.6$ mmol/l.

The final value of the glycemic index of all consumed food was calculated using equation (2) and found GI=72.3.

For convenience, the values of consumed food glycemic index calculated in accordance with the claimed invention are summarized in Table 1.2.

TABLE 1.2.

| $\Delta t$, minutes | $\Delta G_{max}$, mmol/l | $C_{sum}$, g | $\Delta G_{max}^{(gl)}$, mmol/l | GI |
|---|---|---|---|---|
| 37 | 3.4 | 66.0 | 4.6 | 72.3 |

The relative deviation of food GI calculated in accordance with the claimed invention compared to the results obtained by calculating food GI using confirmatory method was 2.8%.

Example 2

Volunteer: a male, age 58, height 174 cm, weight 84 kg.
Nutritional load composition:
carbonade—100 g (carbohydrates—0.0 g);
wheat bread—54 g (carbohydrates—40.9 g, GI—85);
butter—20 g (carbohydrates—0.18 g, GI—70); coffee—160 ml with sugar—10 g (carbohydrates—10 g, GI—70).

Table 2.1 below shows the initial data and calculated value of consumed food glycemic index obtained using the confirmatory method.

TABLE 2.1.

| Food composition | Carbohydrates, g | Carbohydrate content | Product GI | Contribution to mixed nutritional load GI |
|---|---|---|---|---|
| Wheat bread | 40.9 | 0.80 | 85 | 0.80 · 85 = 68.0 |
| Butter | 0.18 | 0.005 | 70 | 0.05 · 70 = 0.35 |
| Coffee with granulated sugar | 10.0 | 0.195 | 70 | 0.195 · 70 = 13.65 |
| Total | 51.1 | 1.0 | | 82.1 |

The calculation of glycemic index in accordance with the claimed invention yielded the following results.

Figure 3:
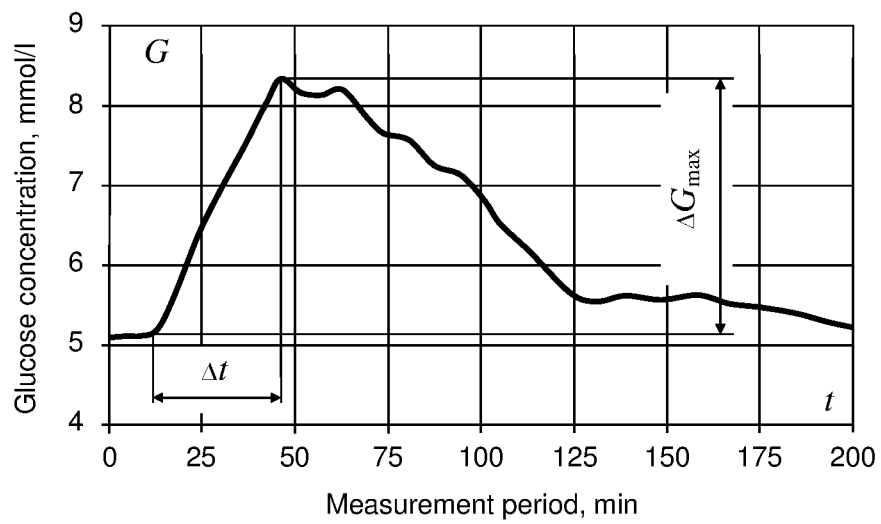
FIG. 3 shows blood glucose concentration measurement results for the second implementation of the invention.

FIG. 3 shows a plot of blood glucose concentration G from the beginning of the meal, while the values of glycemic index determined in accordance with the claimed invention are summarized in Table 2.2.

TABLE 2.2

| $\Delta t$, minutes | $\Delta G_{max}$, mmol/l | $C_{sum}$, g | $\Delta G_{max}^{(gl)}$, mmol/l | GI |
|---|---|---|---|---|
| 38 | 3.1 | 61.8 | 4.1 | 75.6 |

The relative deviation of food GI calculated in accordance with the claimed invention compared to the results obtained by calculating food GI using confirmatory method was 7.7%.

Example 3

Volunteer: a female, age 22, height 162 cm, weight 53 kg.
Nutritional load composition:
Kievskaya cutlet—117 g (carbohydrates—30.4 g, GI—85);
Boiled buckwheat—125 g. (carbohydrates—31.2 g, GI—40);
Coffee with granulated sugar—160 ml (carbohydrates—5 g, GI—70).

Table 2.1 below shows the initial data and calculated value of consumed food glycemic index obtained using the confirmatory method.

TABLE 3.1

| Food composition | Carbohydrates, g | Carbohydrate content | Product GI | Contribution to mixed nutritional load GI |
|---|---|---|---|---|
| Kievskaya cutlet | 30.4 | 0.46 | 85 | 0.46 · 85 = 39.1 |
| Boiled buckwheat | 31.2 | 0.47 | 40 | 0.47 · 40 = 18.8 |
| Coffee with granulated sugar | 5.0 | 0.07 | 70 | 0.07 · 70 = 4.9 |
| Total | 66.7 | 1.0 | | 62.8 |

The calculation of glycemic index in accordance with the claimed invention yielded the following results.

Figure 4:
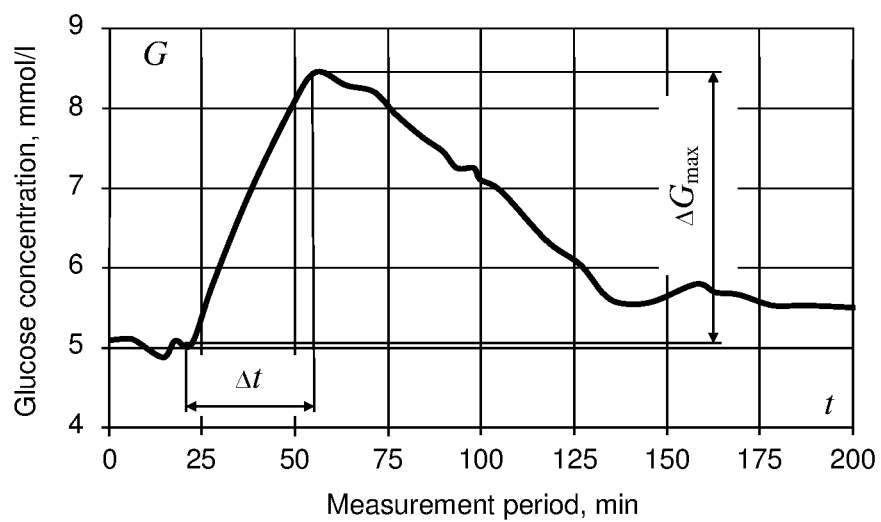
FIG. 4 shows blood glucose concentration measurement results for the third implementation of the invention.

FIG. 4 shows a plot of blood glucose concentration G from the start of the meal, while the results of determining the glycemic index of the present invention are summarized in Table 3.2.

TABLE 3.2.

| $\Delta t$, minutes | $\Delta G_{max}$, mmol/l | $C_{sum}$, g | $\Delta G_{max}^{(gl)}$, mmol/l | GI |
|---|---|---|---|---|
| 39 | 3.25 | 66.5 | 4.64 | 70.0 |

The relative deviation of food GI calculated in accordance with the claimed invention compared to the results obtained by calculating food GI using confirmatory method was 4.9%.

Tests proved that the method proposed in the claimed invention can provide an estimate of the glycemic index of mixed or, in other words, real food assimilated by a human body. The glycemic index evaluation performed using this method takes into consideration the peculiarities of particular food assimilation by a person. Moreover, the resulting glycemic index of consumed food is obtained immediately after the food intake ends.

The proposed method is intended primarily for determining the glycemic index of a mixed food assimilated by a healthy human and can be used for developing various devices and systems for automatic monitoring of carbohydrate content of human food.

What is claimed is:
1. A method for determining a glycemic index of multicomponent food consumed by a human, the method comprising:

measuring a blood glucose concentration in the human from an onset of increase of a blood glucose concentration caused by intake of the food by the human until the blood glucose concentration reaches its peak;

using measurements obtained in the previous step to measure a time interval $\Delta t$ from the onset to the peak of the blood glucose concentration, to determine a maximum increase of a blood glucose concentration $\Delta G_{max}$ over the time interval $\Delta t$, and to calculate a carbohydrate content Csum of the food consumed by the human, wherein the carbohydrate content $C_{sum}$ is = $K \cdot \Delta t \cdot \Delta G_{max}$, and wherein a proportionality factor K ranges from 0.35 to 0.6 g/min·mmol/l; and determining the glycemic index of the food consumed by the human as a ratio $\Delta G_{max} / \Delta G^{(gl)}_{max}$, wherein $\Delta G^{(gl)}_{max}$ is a maximum presumptive increase of a blood glucose concentration upon intake by the human of pure glucose in an amount equal to the carbohydrate content $C_{sum}$.

2. The method of claim 1, wherein the proportionality factor is K=0.525 g/min·mmol/l.

3. The method of claim 2, wherein the food included 51.1-69.7 g of carbohydrates.

4. The method of claim 1, wherein measuring the blood glucose concentration in the human is done non-invasively.

* * * * *